US008128661B2

(12) United States Patent
Zucherman et al.

(10) Patent No.: US 8,128,661 B2
(45) Date of Patent: Mar. 6, 2012

(54) INTERSPINOUS PROCESS DISTRACTION SYSTEM AND METHOD WITH POSITIONABLE WING AND METHOD

(75) Inventors: James F. Zucherman, San Francisco, CA (US); Ken Y. Hsu, San Francisco, CA (US); Charles J. Winslow, Walnut Creek, CA (US); Henry A. Klyce, Piedmont, CA (US); John J. Flynn, Walnut Creek, CA (US)

(73) Assignee: Kyphon Sarl, Neuchatel (CH)

( * ) Notice: Subject to any disclaimer, the term of this patent is extended or adjusted under 35 U.S.C. 154(b) by 365 days.

(21) Appl. No.: 12/559,295

(22) Filed: Sep. 14, 2009

(65) Prior Publication Data
US 2010/0004744 A1 Jan. 7, 2010

Related U.S. Application Data

(63) Continuation of application No. 10/747,534, filed on Dec. 29, 2003, now abandoned, which is a continuation of application No. 10/014,118, filed on Oct. 26, 2001, now Pat. No. 6,695,842, which is a continuation-in-part of application No. 09/799,215, filed on Mar. 5, 2001, now Pat. No. 7,101,375, which is a continuation-in-part of application No. 09/473,173, filed on Dec. 28, 1999, now Pat. No. 6,235,030, which is a continuation-in-part of application No. 09/179,570, filed on Oct. 27, 1998, now Pat. No. 6,048,342, which is a continuation-in-part of application No. 08/958,281, filed on Oct. 27, 1997, now Pat. No. 5,860,977, which is a continuation-in-part of application No. 08/778,093, filed on Jan. 2, 1997, now Pat. No. 5,836,948.

(51) Int. Cl.
*A61B 17/70* (2006.01)

(52) U.S. Cl. ..... 606/248; 606/247; 606/249; 623/17.11; 623/17.16

(58) Field of Classification Search .......... 606/246–279, 606/907; 623/17.11–17.16
See application file for complete search history.

(56) References Cited

U.S. PATENT DOCUMENTS

| | | |
|---|---|---|
| 2,077,804 A | 4/1937 | Morrison |
| 2,677,369 A | 5/1954 | Knowles |
| 3,648,691 A | 3/1972 | Lumb et al. |
| 4,011,602 A | 3/1977 | Rybicki et al. |
| 4,257,409 A | 3/1981 | Bacal et al. |
| 4,554,914 A | 11/1985 | Kapp et al. |

(Continued)

FOREIGN PATENT DOCUMENTS
DE 2821678 A1 11/1979
(Continued)

OTHER PUBLICATIONS

"Dispositivo Intervertebrale Ammortizzante DIAM," date unknown, p. 1.

(Continued)

*Primary Examiner* — Thomas C. Barrett
*Assistant Examiner* — Andrew Yang

(57) ABSTRACT

An implant that is implanted between adjacent spinous processes for the relief of pain associated with the spine. The device has a spacer to distract apart the adjacent spinous processes. To minimize trauma to the patient, the device has a tapered tissue expander to distract a previously created opening between the adjacent spinous processes. The device also has two wings. The position of one wing is adjustable to allow for ease of assembly in a patient.

3 Claims, 7 Drawing Sheets

U.S. PATENT DOCUMENTS

| | | |
|---|---|---|
| 4,573,454 A | 3/1986 | Hoffman |
| 4,604,995 A | 8/1986 | Stephens et al. |
| 4,632,101 A | 12/1986 | Freedland |
| 4,657,550 A | 4/1987 | Daher |
| 4,686,970 A | 8/1987 | Dove et al. |
| 4,827,918 A | 5/1989 | Olerud |
| 4,863,476 A | 9/1989 | Shepperd |
| 4,931,055 A | 6/1990 | Bumpus et al. |
| 4,969,887 A | 11/1990 | Sodhi |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,306,275 A | 4/1994 | Bryan |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,415,661 A | 5/1995 | Holmes |
| 5,437,672 A | 8/1995 | Alleyne |
| 5,454,812 A | 10/1995 | Lin |
| 5,496,318 A | 3/1996 | Howland et al. |
| 5,518,498 A | 5/1996 | Lindenberg et al. |
| 5,554,191 A | 9/1996 | Lahille et al. |
| 5,609,634 A | 3/1997 | Voydeville |
| 5,609,635 A | 3/1997 | Michelson |
| 5,628,756 A | 5/1997 | Barker, Jr. et al. |
| 5,645,599 A | 7/1997 | Samani |
| 5,665,122 A | 9/1997 | Kambin |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,755,797 A | 5/1998 | Baumgartner |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,068,630 A | 5/2000 | Zucherman et al. |
| 6,126,689 A | 10/2000 | Brett |
| 6,127,597 A | 10/2000 | Beyar et al. |
| 6,132,464 A | 10/2000 | Martin |
| 6,190,414 B1 | 2/2001 | Young |
| 6,214,050 B1 | 4/2001 | Huene |
| 6,293,949 B1 | 9/2001 | Justis et al. |
| 6,348,053 B1 | 2/2002 | Cachia |
| 6,352,537 B1 | 3/2002 | Strnad |
| 6,364,883 B1 | 4/2002 | Santilli |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,451,019 B1 | 9/2002 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,758,863 B2 | 7/2004 | Estes et al. |
| 6,761,720 B1 | 7/2004 | Senegas |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,377,942 B2 | 5/2008 | Berry |
| 7,442,208 B2 | 10/2008 | Mathieu et al. |
| 7,445,637 B2 | 11/2008 | Taylor |
| 2002/0143331 A1 | 10/2002 | Zucherman et al. |
| 2003/0153915 A1 | 8/2003 | Nekozuka et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241613 A1 | 10/2006 | Brueneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0293662 A1 | 12/2006 | Boyer, II et al. |
| 2006/0293663 A1 | 12/2006 | Walkenhorst et al. |
| 2007/0043362 A1 | 2/2007 | Malandain et al. |
| 2007/0151116 A1 | 7/2007 | Malandain |
| 2007/0162000 A1 | 7/2007 | Perkins |
| 2007/0198091 A1 | 8/2007 | Boyer et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1 | 11/2007 | Bruneau et al. |
| 2007/0282443 A1 | 12/2007 | Globerman et al. |
| 2008/0161818 A1 | 7/2008 | Kloss et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |

| | | | |
|---|---|---|---|
| EP | 0767636 B1 | 1/1999 | |
| EP | 1004276 A1 | 5/2000 | |
| EP | 1138268 A1 | 10/2001 | |
| EP | 1302169 A1 | 4/2003 | |
| EP | 1330987 A1 | 7/2003 | |
| FR | 2623085 A1 | 5/1989 | |
| FR | 2625097 A1 | 6/1989 | |
| FR | 2681525 A1 | 3/1993 | |
| FR | 2700941 A1 | 8/1994 | |
| FR | 2703239 A1 | 10/1994 | |
| FR | 2707864 A1 | 1/1995 | |
| FR | 2717675 A1 | 9/1995 | |
| FR | 2722087 A1 | 1/1996 | |
| FR | 2722088 A1 | 1/1996 | |
| FR | 2724554 A1 | 3/1996 | |
| FR | 2725892 A1 | 4/1996 | |
| FR | 2730156 A1 | 8/1996 | |
| FR | 2731643 A1 | 9/1996 | |
| FR | 2775183 A1 | 8/1999 | |
| FR | 2799948 A1 | 4/2001 | |
| FR | 2816197 A1 | 5/2002 | |
| JP | 02-224660 | 9/1990 | |
| JP | 09-075381 | 3/1997 | |
| SU | 988281 | 1/1983 | |
| WO | WO 94/26192 | 11/1994 | |
| WO | WO 94/26195 | 11/1994 | |
| WO | WO 98/20939 | 5/1998 | |
| WO | WO 99/26562 | 6/1999 | |
| WO | WO 00/44319 | 8/2000 | |
| WO | WO 01/54598 A1 | 8/2001 | |
| WO | WO 03/057055 A1 | 7/2003 | |
| WO | WO 2004/047689 A1 | 6/2004 | |
| WO | WO 2004/047691 A1 | 6/2004 | |
| WO | WO 2004/084768 A2 | 10/2004 | |
| WO | WO 2005/009300 A1 | 2/2005 | |
| WO | WO 2005/011507 A1 | 2/2005 | |
| WO | WO 2005/044118 A1 | 5/2005 | |
| WO | WO 2005/048856 A1 | 6/2005 | |
| WO | WO 2005/110258 A1 | 11/2005 | |
| WO | WO 2006/064356 A1 | 6/2006 | |
| WO | WO 2007/034516 A1 | 3/2007 | |
| WO | WO 2007052975 A1 | 5/2007 | |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

INTERSPINOUS PROCESS DISTRACTION SYSTEM AND METHOD WITH POSITIONABLE WING AND METHOD

CROSS REFERENCE TO RELATED APPLICATIONS

This application is a continuation of application Ser. No. 10/747,534 filed Dec. 29, 2003 which is a continuation of application Ser. No. 10/014,118 filed Oct. 26, 2001 now U.S. Pat. No. 6,695,842, which is a continuation in part of application Ser. No. 09/799,215 filed Mar. 5, 2001, now U.S. Pat. No. 7,101,375, which is a continuation in part of application Ser. No. 09/473,173, filed Dec. 28, 1999, now U.S. Pat. No. 6,235,030, which is a continuation in part of application Ser. No. 09/179,570 filed Oct. 27, 1998, now U.S. Pat. No. 6,048,342, which is a continuation in part of application Ser. No. 08/958,281 filed Oct. 27, 1997, now U.S. Pat. No. 5,860,977, which is a continuation in part of application Ser. No. 08/778,093 filed Jan. 2, 1997, now U.S. Pat. No. 5,836,948, each of which is incorporated herein by reference in its entirety.

FIELD OF THE INVENTION

The present invention is directed to an interspinous process implant system and method which can, for example, distract apart and maintain said distraction of adjacent spinous process.

BACKGROUND OF THE INVENTION

As the present society ages, it is anticipated that there will be an increase in adverse spinal conditions which are characteristic of older people. By way of example only, with aging comes increases in spinal stenosis (including, but not limited to, central canal and lateral stenosis) the thickening of the bones which make up the spinal column and facet arthropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating these and other spinal conditions, which procedures and implants are minimally invasive, can be tolerated by the elderly and can be performed preferably on an outpatient basis.

SUMMARY OF THE INVENTION

The present invention is directed to providing a minimally invasive apparatus and method for alleviating discomfort associated with the spinal column.

The present invention provides for apparatus and method for relieving pain by relieving the pressure and restrictions on the aforementioned blood vessels and nerves. Such alleviation of pressure is accomplished in the present invention through the use of an implant and method which distract the spinous process of adjacent vertebra in order to alleviate the problems caused by spinal stenosis and facet arthropathy and the like as well as other spinal ailments. While the implant and method particularly address the needs of the elderly, the invention can be used with individuals of all ages and sizes where distraction of the spinous process would be beneficial.

In one aspect of the invention, an implant is provided for relieving pain comprising a device positioned between a first spinous process and a second spinous process. The device includes a spinal column extension stop and a spinal column flexion non-inhibitor.

In a further aspect of the invention, the implant includes a first unit having a body with a guide or tissue expander and a first wing, with the first wing located at a first end of the body. The guide extends from a second end of the body located distally from the first wing. The implant further includes a sleeve or spacer provided over said body. The implant further includes a second wing and a device for securing the second wing to the first unit, wherein the sleeve or spacer is located between the first and second wings.

In yet still a further aspect of the invention the implant includes a sleeve which is rotatable relative to the wings of the implant in order to be able to accommodate the anatomical structure of spinous processes.

In still another aspect of the invention, the implant includes a second wing that is movable toward the first wing after the second wing is assembled to the first unit in the patient. In this aspect a fastener can be operated to cause the second wing to move toward the first wing. Accordingly, the implant can be easily assembled in the patient without concern for the shape of the spinous processes and then the first and second wings can be drawn together so that these wings are positioned closer to the spinous processes.

In another aspect of the invention, the second wing includes an alignment tab which is received in an alignment groove of the first unit in order to guide the second wing as it is urged toward the first wing.

In another aspect of the invention, a ramp mechanism is used to urge the second wing, toward the first wing.

Other implants and methods within the spirit and scope of the invention can be used to relieve pain associated with the spine and/or increase the volume of the spinal canal thereby alleviating restrictions on vessels and nerves associated therewith and associated pain.

DETAILED DESCRIPTION OF THE INVENTION

Figure 1:
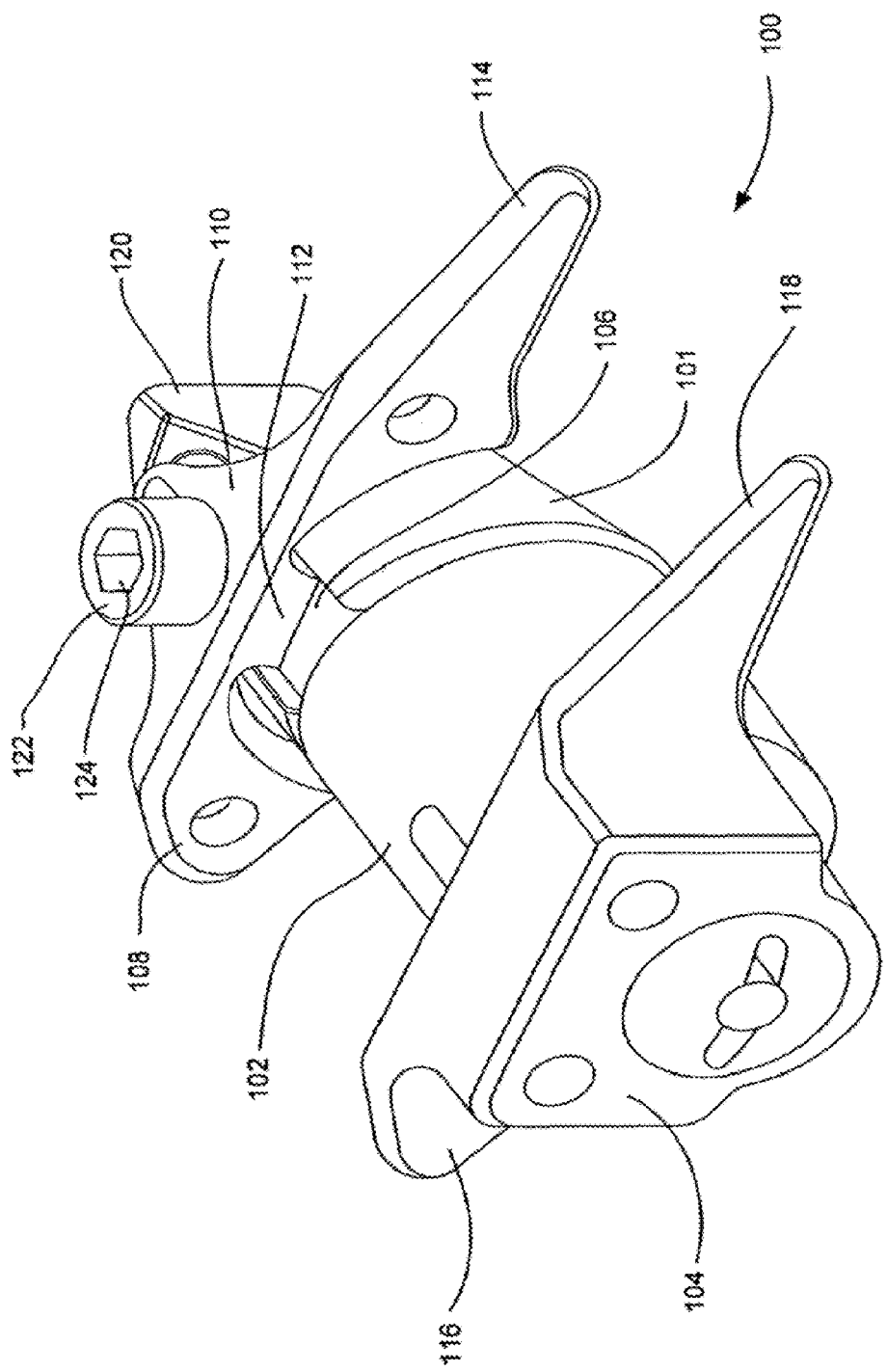
FIG. 1 is a perspective view of an embodiment of the present invention.

Referring to FIG. 1, the implant device 100 has a main body 101. The main body 101 includes a spacer 102, a first wing 104, a tapered front end, lead-in guide or tissue expander 120 and an alignment track 106. The main body 101 is inserted between adjacent spinous processes. Preferably, the main body 101 remains safely and permanently in place without attachment to the bone or ligaments. All of the components of the implant device 100 are made of biologically acceptable material such as, but are not limited to, high strength titanium alloy or stainless steel. Preferably the first wing 104 is laser welded to the main body 101.

The tip of the tissue expender 120 has the smallest diameter, allowing the tip to be inserted into a small initial dilated opening. The diameter and/or cross-sectional areas of the tissue expander 120 then gradually increases until it is substantially similar to the diameter of the main body 101 and spacer 102. The tapered front end 120 makes it easier for a physician to urge the implant device 100 between adjacent spinous processes. When urging the main body 101 between adjacent spinous processes, the front end 120 distracts the adjacent spinous processes to the diameter of the spacer 102. As shown in FIG. 1, the tissue expander 120 is a pyramid shape. In another embodiment the tissue expander preferably has an angle of twenty-five degrees that allows it to clear the facet. This reduces the length of the front end 120. One will appreciate that the shape of the tissue expander 120 can be other shapes such as, but not limited to, cone shaped, or any other shape with a small lead-in cross-section expanding into a larger cross-section. These types of shapes gradually distract the spinous processes to a sufficient distance so that the spacer 102 can conveniently fit between the spinous processes.

The spacer 102 can be made of stainless steel, titanium, a super-elastic material or silicone or other biologically acceptable material. The material can be rigid or resilient as desired. As shown in FIG. 1, the spacer 102 is an elliptically shaped cylinder. One will appreciate that the spacer can consist of other shapes such as, but not limited to, egg-shaped, round-shaped or saddle-shaped. For example, the spacer 102 can be saddle-shaped along the surface which engages the spinous processes so that the high edges and the lower central portions can more fully accommodate the shape of the spinous processes. Preferably, the spacer 102 can swivel, allowing the spacer 102 to self-align relative to the uneven surface of the spinous process. This ensures that compressive loads are distributed equally on the surface of the bone. By way of example only, the spacer 102 can have diameters of six millimeters, eight millimeters, ten millimeters, twelve millimeters and fourteen millimeters. These diameters refer to the height by which the spacer distracts and maintains apart the spinous process. Thus for an elliptical spacer the above selected height would represent the small diameter measurement from the center of the ellipse. The largest diameter would be transverse to the alignment, of the spinous process, one above the other. Smaller and larger diameters are within the scope of the invention.

The shape of the spacer 102 and for that matter the shape of the entire implant is such that for purposes of insertion between the spinous processes, the spinous processes do not need to be altered or cut away in any manner in order to accommodate the implant 100. Additionally, the associated ligaments do not need to be cut away and there would be very little or no damage to the other adjacent or surrounding tissues other than piercing through and separating, or dilating an opening in a ligament.

The first wing 104 has a lower portion 116 and an upper portion 118. The upper portion 118 is designed to preferably accommodate, in this particular embodiment, the anatomical form or contour of the L4 (for an L4-L5 placement) or L5 (for an L5-S1 placement) vertebra. It is to be understood that the same shape or variations of this shape can be used to accommodate other vertebra. The lower portion 116 is also rounded to accommodate, in a preferred embodiment, the vertebra. The lower portion 116 and upper portion 118 of the first wing 104 will act as a stop mechanism when the implant device 100 is inserted between adjacent spinous processes. The implant device 100 cannot be inserted beyond the surfaces of the first wing 104. Additionally, once the implant device 100 is inserted, the first wing 104 can prevent side-to-side, or posterior to anterior movement of the implant device 100.

The implant device 100 also has an adjustable wing 110. The adjustable wing 110 has a lower portion 108 and an upper portion 114. Similar to the first wing 104, the adjustable wing 110 is designed to accommodate the anatomical form or contour of the vertebra.

The adjustable wing 110 is secured to the main body 101 with a fastener 122 provided through tapered cavity 130. The adjustable wing 110 also has an alignment tab 112. When the adjustable wing 110 is initially placed on the main body 101, the alignment tab 112 engages the alignment track 106. The alignment tab 112 slides within the alignment track 106 and helps to maintain the adjustable wing 110 substantially parallel with the first wing 104 in this preferred embodiment. When the main body 101 is inserted into the patient and the adjustable wing 110 has been attached, the adjustable wing 110 also can prevent side-to-side, or posterior to anterior movement.

Figure 2:
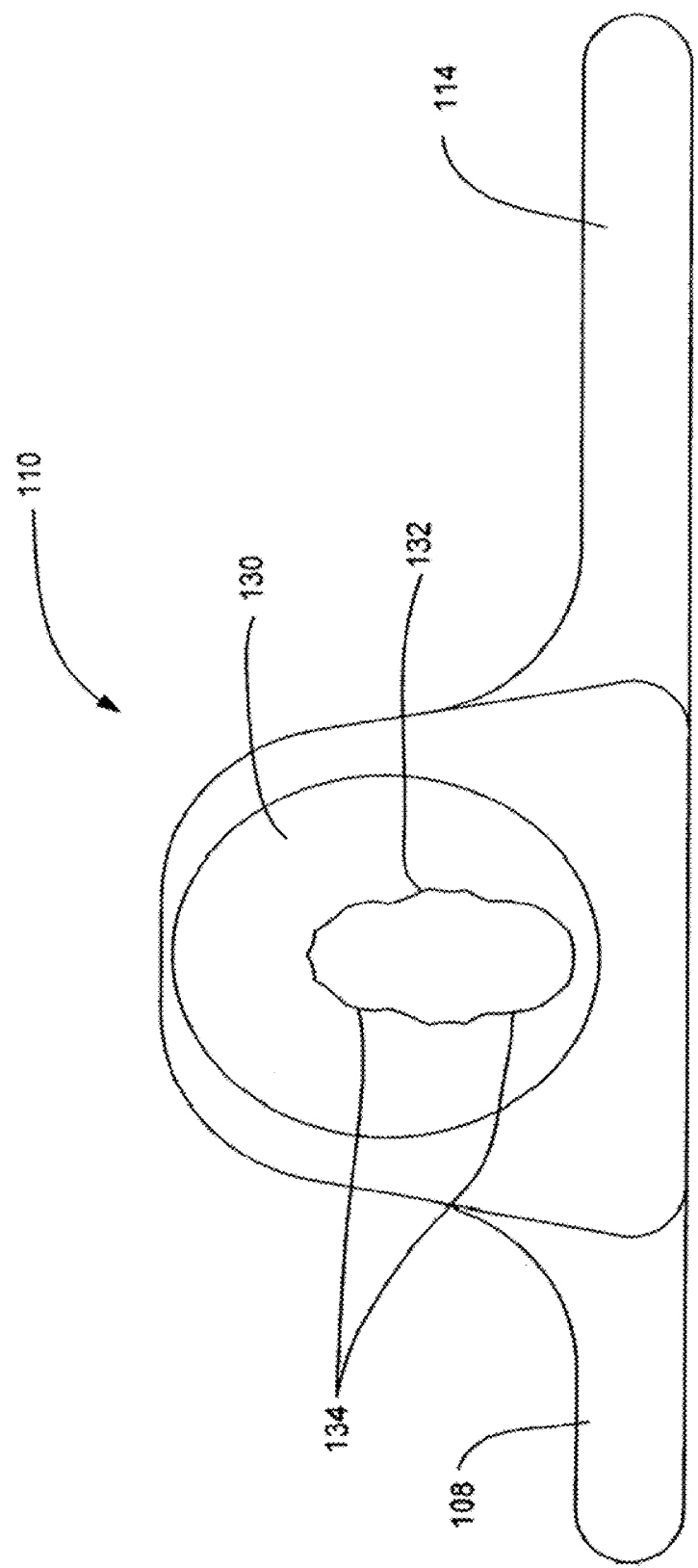
FIG. 2 is a top view of an embodiment of the adjustable wing of the present invention.

Referring now to FIG. 2, the adjustable wing 110 includes the above mentioned tapered cavity 130. The tapered cavity 130 has a middle portion 132, two end portions 134 and a tapered wall 131. The diameter of the middle portion 132 is larger than the diameter of either end portion 134. The tapered wall 131 has a larger diameter at the top surface of the adjustable wing 110 than at the bottom surface. Accordingly a cone-like shape is formed. When the fastener 122 engages the main body 101 and is rotated, the fastener 122 travels into the main body 101 (see FIG. 1). As the fastener 122 travels into the main body 101, the adjustable wing 110 will travel along the alignment track 106 towards the first wing 104. The alignment tab 112 engages the alignment track 106 and functions as a guide, keeping the adjustable wing 110 and the first wing 104 substantially parallel to each other.

Figure 3:
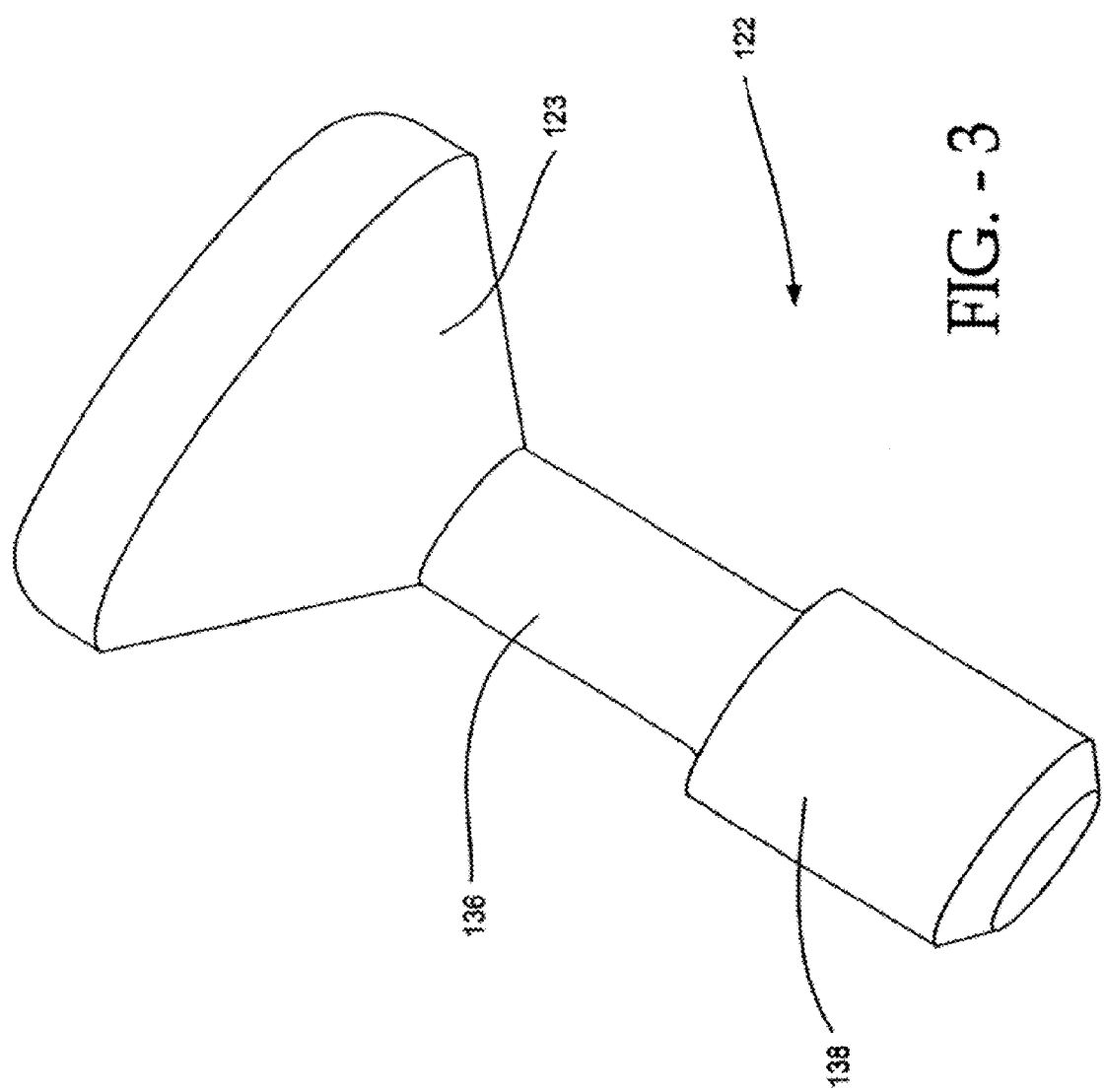
FIG. 3 is a perspective view of an embodiment of the fastener used in the present invention.

The fastener 122 has a tapered head 123, a middle section 136 and a threaded bottom section 138 (see FIG. 3). The top end of the tapered head 123 has a diameter substantially similar to the diameter of the top surface of the tapered cavity 130. The diameter of the tapered head 123 is reduced as the tapered head meets the middle section 136. The slope of the tapered head 123 is similar to the slope of the tapered cavity 130 of the adjustable wing 110. The middle section 136 has a diameter substantially similar to the end portions 134 of the adjustable wing 110. The threaded bottom section 138 has a slightly larger diameter than the middle section 136 and is in one embodiment slightly smaller than the diameter of the middle portion 132 of the adjustable wing 110.

As the diameter of the end portions 134 is smaller than the diameter of the bottom section 138, the fastener 122 cannot initially be placed through the end portions 134 of the adjustable wing 110. Accordingly, to fasten the adjustable wing 110 to the main body 101, the threaded bottom section 138 of the fastener 122 is placed through the middle portion 132 of the adjustable wing 110 and into the main body 101. With a turn of the fastener 122, the threaded portion of the bottom section 138 will engage the main body 101.

In another preferred embodiment the diameter of threaded bottom section 138 is larger than the diameter of the middle portion of the adjustable wing 110. For this embodiment, the fasteners 122 are inserted into the cavity 130 by slicing the cavity 130 (FIG. 2) through the thinnest portion of the wall, spreading the wall open, inserting the middle section 136 in the cavity with the threaded bottom section 138 projection below the cavity 130, and laser welding the wall closed. The slicing step preferably includes using a carbide slicing device.

Figure 4:
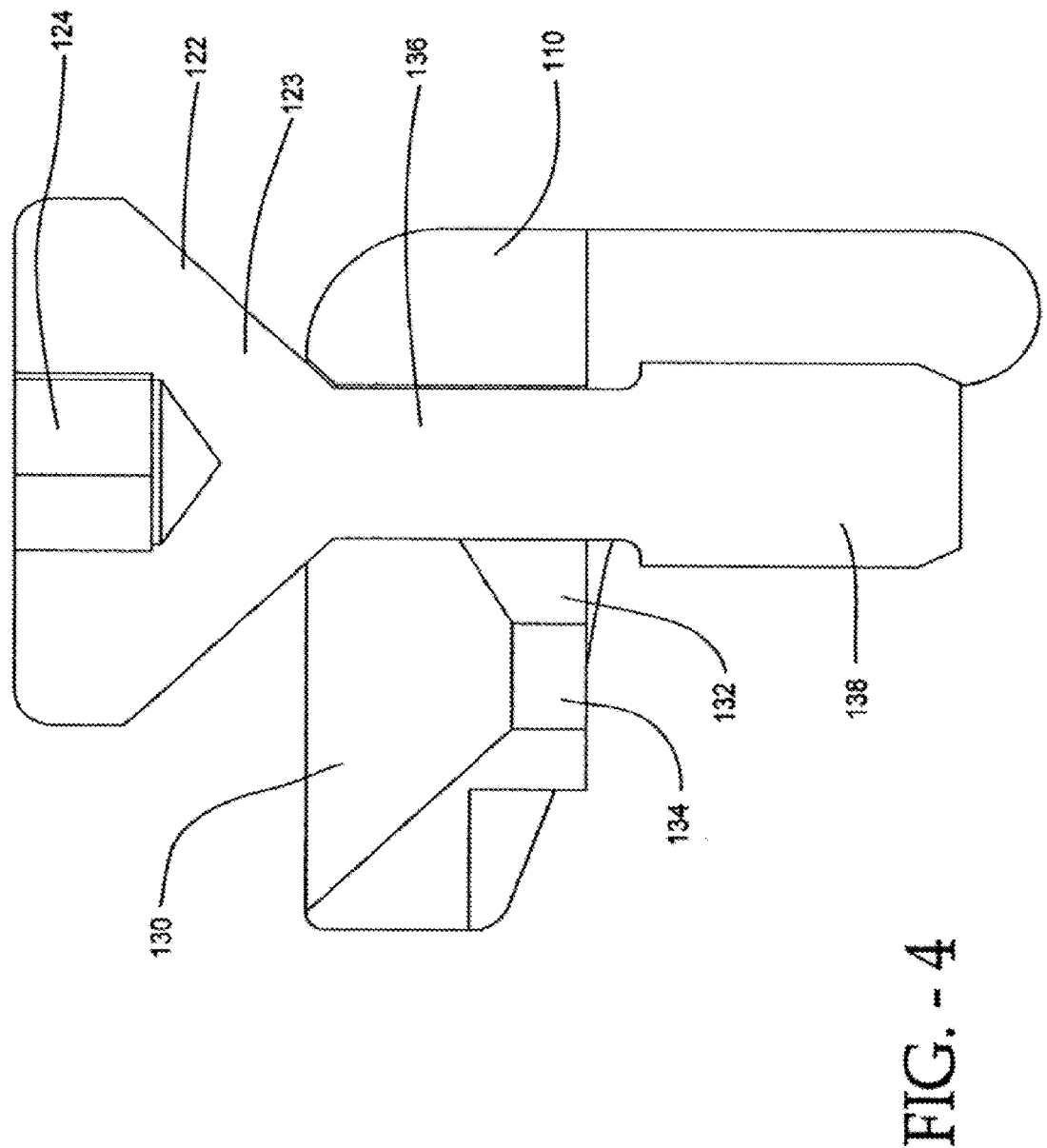
FIG. 4 is cut-away view illustrating the interaction between the fastener and the adjustable wing with the adjustable wing in a first position.

When the adjustable wing 110 is in the position furthest from the position of the first wing 104, the tapered head 123 of the fastener 122 is substantially out of, and not engaging, the tapered cavity 130 of the adjustable wing 110 (See FIG. 4). As the fastener 122 is rotated, the fastener 122 will continue to engage, and travel further into, the main body 101. As the fastener 122 travels downwardly into the main body 101, the tapered head 123 of the fastener 122 contacts the wall 131 of the tapered cavity 130. The adjustable wing 110 can freely slide back and forth, limited by the end portions 134 of the tapered cavity 130. When the tapered head 123 contacts the wall 131 of the tapered cavity 130, the adjustable wing 110 moves toward the first wing 104 guided by the alignment tab 112 in the alignment track 106. Therefore, the adjustable wing 110 remains substantially parallel to the first wing 104 in this preferred embodiment as the adjustable wing 110 moves toward the first wing 104 (see FIG. 5). It is to be understood that the tab 112 and the track 106 can be eliminated in another embodiment of the invention.

Figure 5:
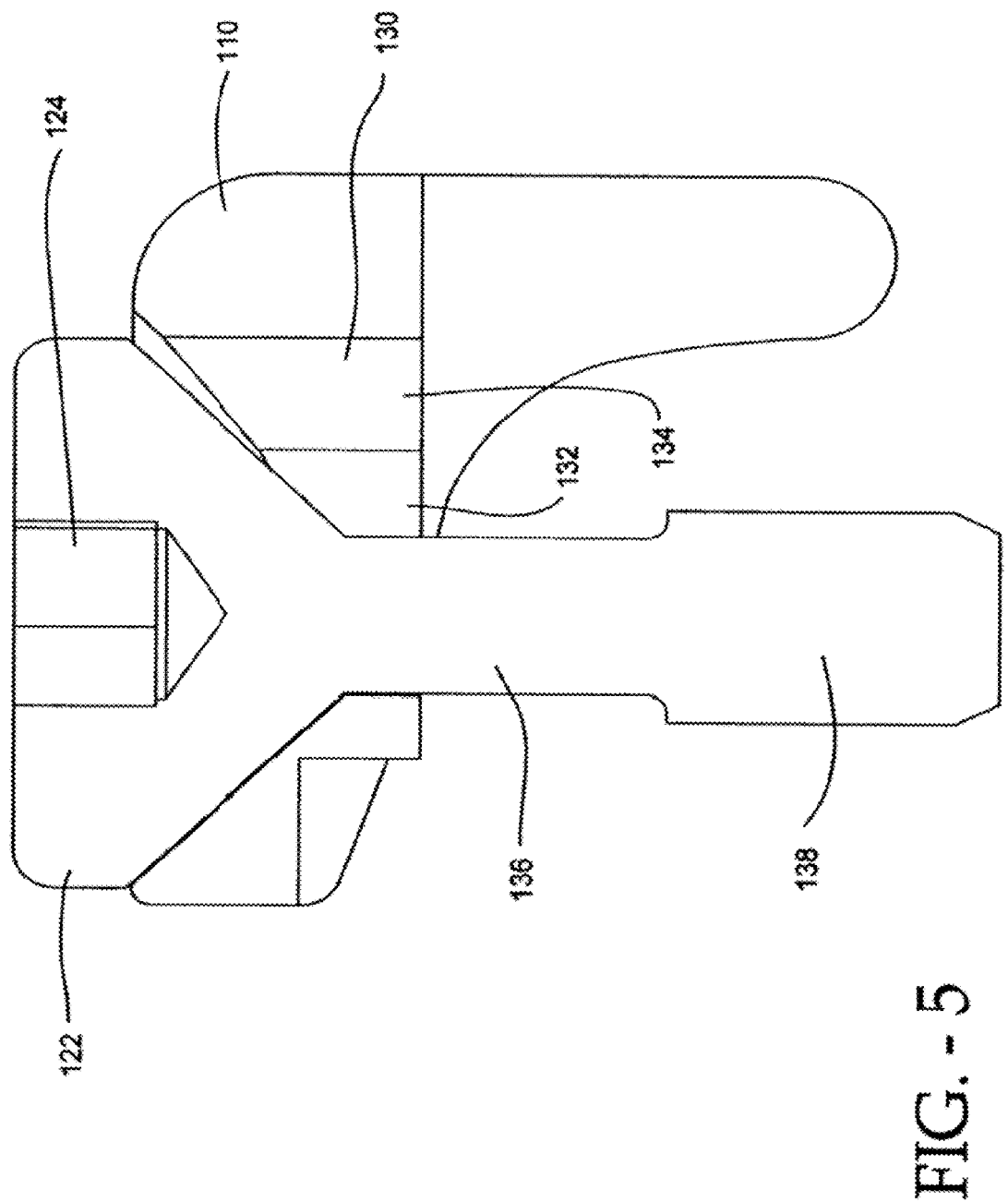
FIG. 5 is a cut-away view illustrating the fastener engaging the adjustable wing with the adjustable wing in a second position.

As shown in FIG. 5, the tapered head of 123 of the fastener 122 is mated in the tapered wall 131 of the adjustable wing 110. Accordingly, with this ramp mechanism, the adjustable wing 100 is urged toward the spinous processes and the first wing 104 and is locked in position, at its closest approach to the first wing 104. This arrangement allows the surgeon to loosely assemble the implant in the patient and then urge the adjustable wing closer to the first wing, by rotating fastener 122 into body 110 making the implanting method more tolerant to the anatomy of the patient.

The structure of the spine is of course unique for every patient. Accordingly if the width of the spinous processes is excessive, the adjustable wing can be left in a position that is between that shown in FIG. 4 and that shown in FIG. 5. The separation between the first wing 104 and the adjustable wing 110 can be incrementally adjusted by the number of turns of the fastener 122.

Figure 6:
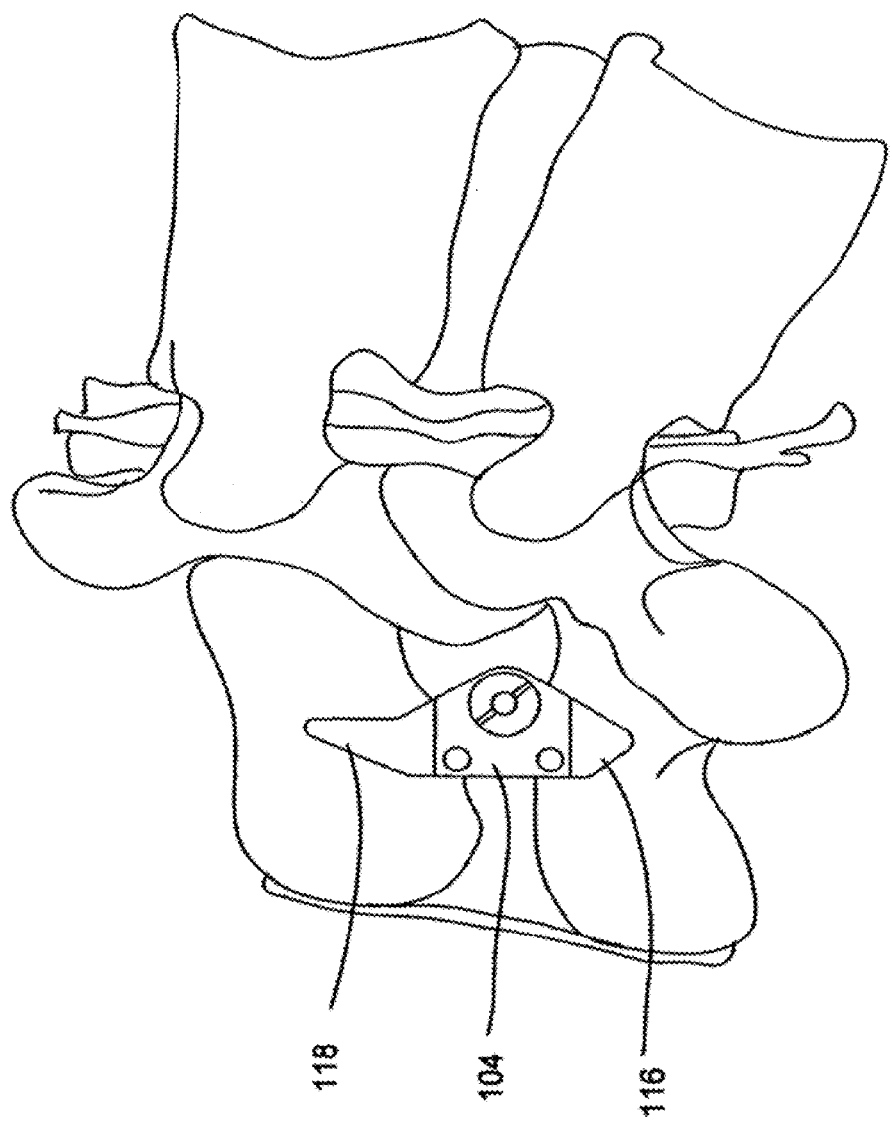
FIG. 6 is a side view illustrating an embodiment of the present invention as implanted between adjacent spinous processes.
Figure 7:
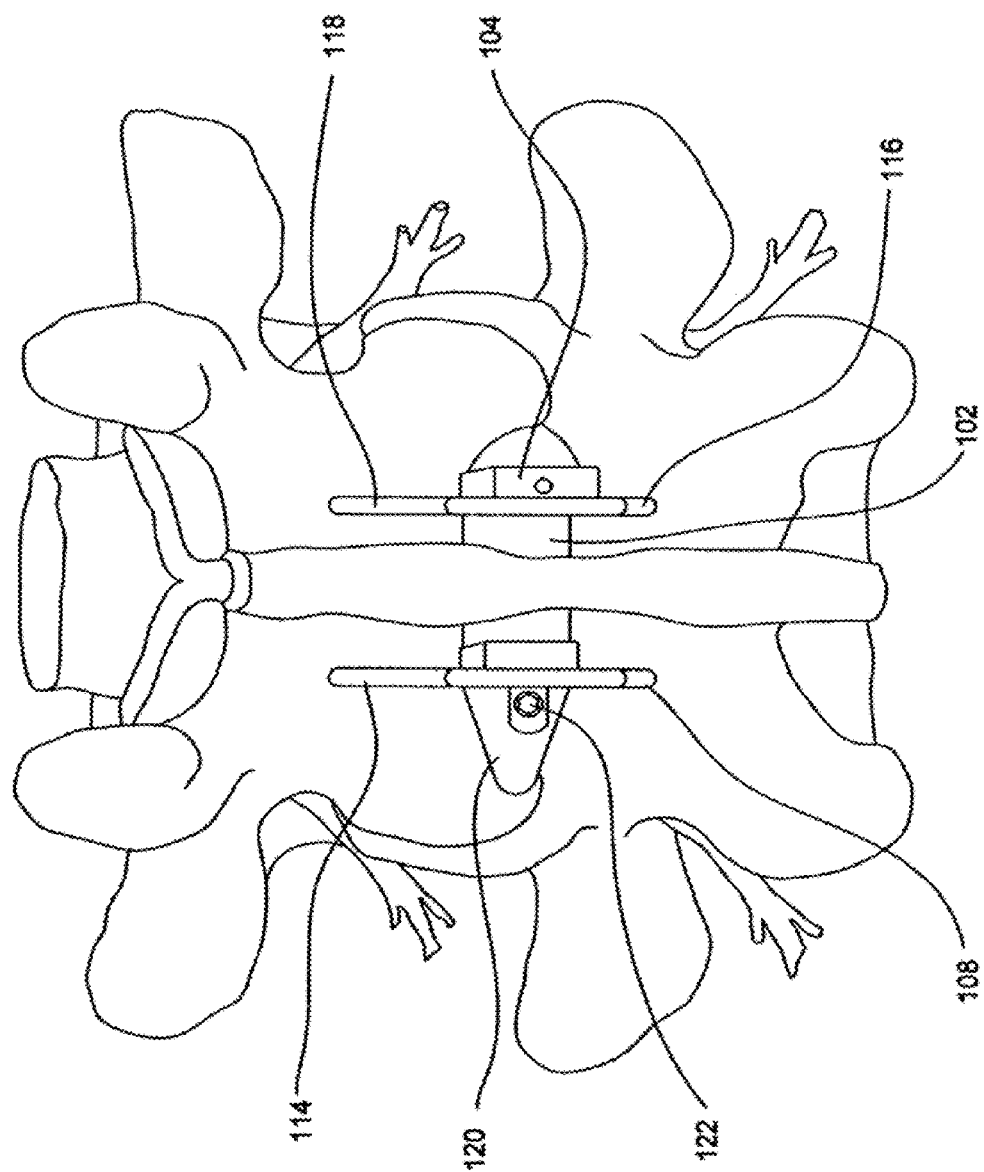
FIG. 7 is a front view of an embodiment of the present invention as implanted between adjacent spinous processes.

FIGS. 6 and 7 illustrate the position of the implant device 100 in a patent. As shown by FIG. 6, the lower portion 116 and upper portion 118 of the first wing 104 function to prevent side-to-side movement, toward and away from the vertebral body ensuring that the implant device 100 remains in place. Similarly, the adjustable wing 110 will also prevent excessive side-to-side movement. The wing also prevents motion in the direction of the main body into the space between the spinous processes.

The foregoing description of preferred embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A spinal implant for positioning between adjacent spinous processes, comprising:
    a main body extending along a longitudinal axis from a proximal end portion thereof to a distal end portion thereof, said main body comprising:
        a spacer adapted to abut adjacent spinous processes oriented transverse to said axis;
        a first wing disposed proximate the proximal end portion and extending outward, transverse to said axis, beyond said spacer;
        a second wing moveably coupled to the main body proximate said distal end portion and extending outward, transverse to said axis, beyond said spacer; said second wing including a first inclined bearing surface disposed at a non-parallel acute angle relative to said axis;
        a securing member engaging said main body so as to couple said second wing to said main body; said securing member including a second inclined bearing surface disposed at a non-parallel acute angle relative to said axis;
        said first bearing surface engaging said second bearing surface so as to limit movement of said second wing away from said proximal end portion;
        wherein displacement of said securing member toward said main body causes said first and second bearing surfaces to be displaced relative to each other and said second wing to be displaced toward said first wing.

2. The spinal implant of claim 1 further comprising a tissue expander disposed proximate said distal end portion that expands toward said proximal end portion; said securing member disposed closer to said tissue expander than a portion of said second wing disposed closest to said first wing.

3. The spinal implant of claim 1 wherein said spacer is rotatably mounted relative to said first wing so as to be rotatable about said longitudinal axis.

\* \* \* \* \*